United States Patent
Furushima et al.

(10) Patent No.: US 7,161,038 B2
(45) Date of Patent: Jan. 9, 2007

(54) PROCESS FOR PRODUCING POLYOXYALKYLENE TRIAMINE

(75) Inventors: Tetsuaki Furushima, Wakayama (JP); Masaharu Jono, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/897,008

(22) Filed: Jul. 23, 2004

(65) Prior Publication Data
US 2005/0027141 A1    Feb. 3, 2005

(30) Foreign Application Priority Data
Jul. 30, 2003    (JP) ............................ 2003-282482

(51) Int. Cl.
*C07C 209/16* (2006.01)
(52) U.S. Cl. ...................... 564/474; 564/480
(58) Field of Classification Search .................. None
See application file for complete search history.

(56) References Cited

U.S. PATENT DOCUMENTS

| 3,347,926 A | 10/1967 | Zech |
| 4,774,263 A | 9/1988 | Weber et al. |
| 5,015,773 A * | 5/1991 | Dobson ....................... 564/474 |
| 5,696,293 A * | 12/1997 | Phillips et al. .............. 564/480 |

FOREIGN PATENT DOCUMENTS

| EP | 0081 701 | 6/1983 |
| EP | 0 284 398 A2 | 9/1988 |
| EP | 0 356 046 A2 | 2/1990 |
| EP | 0 356 047 | 2/1990 |
| GB | 2175910 | 12/1986 |
| JP | 49-14158 | 4/1974 |
| JP | 49-14159 | 4/1974 |
| JP | 1-40048 | 8/1989 |
| JP | 7-3009 | 1/1995 |

OTHER PUBLICATIONS

Fischer et al., Catalysis Today (1997), vol. 37, p. 167-189.*

* cited by examiner

*Primary Examiner*—Brian Davis
(74) *Attorney, Agent, or Firm*—Oblon, Spivak, McClelland, Maier & Neustadt, P.C.

(57) ABSTRACT

The present invention is a process for producing polyoxyalkylene triamine by bringing polyoxyalkylene triol having at its terminal a hydroxyl group into contact with ammonia and hydrogen in the presence of a catalyst comprising ruthenium metal at an amount of 0.5 to 20% by weight of the total of the catalyst, the ruthenium metal being carried on at least one carrier selected from alumina, silica, silica-alumina, titanium dioxide, and titanium dioxide-silica.

20 Claims, No Drawings

PROCESS FOR PRODUCING POLYOXYALKYLENE TRIAMINE

FIELD OF THE INVENTION

The present invention relates to a process for producing polyoxyalkylene triamine, which is industrially useful, for example, as paint and a curing agent for molded material.

BACKGROUND OF THE INVENTION

Polyoxyalkylene triamine is widely used as a curing agent for epoxy resin, or a raw material of polyamides. As the process for producing the same, there is known a process of using a catalyst to cause the corresponding polyoxyalkylene triol as a raw material to react directly with ammonia and hydrogen. It is generally considered that in this direct amination reaction using the polyoxyalkylene triol as a raw material, the reaction advances along the step (1) of the generation of aldehyde and/or ketone groups by dehydrogenation from the hydroxyl groups, the step (2) of the addition of ammonia, the step (3) of the generation of imino groups by dehydration, and the step (4) of the conversion of the imino groups to amino groups by the addition of hydrogen. In order to improve the reactivity and selectivity in the successive steps, there has been suggested a catalyst containing a nickel component, or some other catalyst as a catalyst for catalytic reduction.

For example, U.S. Pat. No. 3,347,926 discloses a process of using a Raney(sponged) nickel catalyst into which a small amount of chromium is incorporated to produce an aliphatic amine from a raw material containing hydroxyl groups. In JP-B 1-40048, polyoxyalkylene diol is caused to react in the presence of an ordinary Raney(sponged) nickel catalyst. GB-B 2175910 describes a circulating-manner process for producing polyoxyalkylene diamine using a Raney (sponged) nickel catalyst to which molybdenum is added. EP-A 81701 and U.S. Pat. No. 4,774,263 discloses reaction of polyoxyalkylene triol having a molecular weight of 6000 in the presence of a Raney(sponged) nickel catalyst.

In the meantime, EP-A 356047 and JP-A 7-3009 disclose processes of using a catalyst on which two or more kinds of ruthenium and other transition metals are carried to produce polyoxyalkylene diamine.

JP-B 49-14158 and JP-B 49-14159 disclose reaction between a propylene oxide polymer and ammonia using a carbon catalyst on which ruthenium is carried.

SUMMARY OF THE INVENTION

The present invention provides a process for producing polyoxyalkylene triamine by bringing polyoxyalkylene triol having at its terminal a hydroxyl group into contact with ammonia and hydrogen in the presence of a catalyst, the catalyst including ruthenium metal at an amount of 0.5 to 20% by weight of the total of the catalyst, carried on at least one carrier selected from alumina, silica, silica-alumina, titanium dioxide, and titanium dioxide-silica.

DETAILED DESCRIPTION OF THE INVENTION

In JP-B 1-40048, the conversion rate and the selectivity of a desired product are low.

GB-B 2175910 has problems that the catalyst thereof is not yet sufficiently active; an LHSV of 0.1 to 2.0 (as the LHSV, which is the time space velocity of liquid is higher, the reaction time is shorter) and a high pressure (a pressure over 13 MPa in a continuous manner) are required in order to use this catalyst for converting the hydroxyl groups directly to amino groups; and the process is not easily carried out on an industrial scale.

In the EP-A 81701, conditions for the reaction are severe, and the conversion rate is only 80%. Thus, the productivity and the quality are insufficient.

In the meantime, EP-A 356047 and JP-A 7-3009 have a problem that the processes therein are unsuitable for mass-production since the amount of hydrogen and ammonia handled in the reaction is large. In particular, in the case that a compound having in the molecule thereof three or more hydroxyl groups is used as a raw material, the large mole ratio of ammonia to the hydroxyl groups is required. Therefore, a low pressure is not easily kept at high temperatures. As a result, a technique suitable for the industrialization thereof has not yet been constructed.

The present invention provides a process for producing polyoxyalkylene triamine which can be for example applied to a batch process or a continuous process, and has benefits such as having sufficient activity and selectivity in a low-pressure reaction, requiring no aid for improving the selectivity, not easily being affected by catalyst poison, such as water, and giving a high conversion rate and selectivity under the reaction condition that the mole ratio of ammonia to hydroxyl groups is relatively small.

The production process of the present invention uses polyoxyalkylene triol as a raw material, is applicable to a continuous process or a batch process, and makes it possible for example to produce polyoxyalkylene triamine which is good in color tone stability with a high conversion rate at a low pressure, at which the handling is easy, under the condition that the mole ratio of hydrogen and ammonia to the hydroxyl groups is relatively small.

In the production of the present invention, it is preferably unnecessary to remove generated water to the outside of the reaction system. The OH group of the triol compound is reacted with ammonia, wherein the ammonia is consumed and the pressure of the reactor decrease. As a result, the reactivity and selectivity of the reaction of the triol compound with ammonia to produce the amino compound is occasionally decreased. In this case, by supplying hydrogen gas in the reactor, however, the pressure in the reactor is maintained. Thus, the amino compound can be prepared with high activity and high selectivity.

The polyoxyalkylene triol having at its terminal a hydroxyl group, which is in the used present invention, may be a product obtained by adding alkylene oxide to glycerin, or some other triol. A compound represented by formula (I) is preferable:

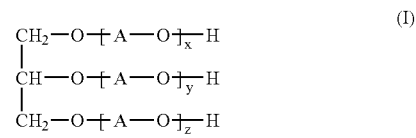

(I)

(In formula (I), A represents a normal or branched alkylene group having 2 to 6 carbon atoms, in the compound represented by formula (I), "A" may be the same as or different from one another, x, y and z are each an average mole number of alkyleneoxy groups added to each oxygen atom, and the total of x+y+z is from 1 to 100.)

The polyoxyalkylene triamine obtained by a preferred process of the present invention preferably contains 85% or more by weight of a compound represented by formula (II):

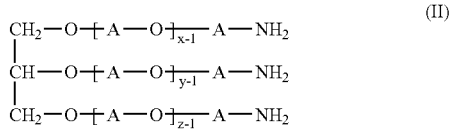

(In the formula, A, x, y and z represent the same meanings as described above.)

In formulae (I) and (II), A is preferably an alkylene group having 2 to 3 carbon atoms. The molecular weight of the polyoxyalkylene triol used in the present invention is preferably from 1500 to 5000.

The catalyst used in the present invention contains ruthenium metal at an amount of 0.5 to 20% by weight, preferably 0.5 to 10% by weight of the total of the catalyst from the viewpoint of obtaining sufficient catalyst activity and good selectivity and conversion rate. The ruthenium catalyst in the present invention is carried on at least one carrier selected from alumina, silica, silica-alumina, titanium dioxide, and titanium dioxide-silica. The carrier is preferably alumina, γ-alumina, silica or silica-alumina, more preferably alumina or γ-alumina.

In the present invention, a mixed catalyst can be used which is composed of a ruthenium catalyst as described above and a catalyst that contains at least one metal selected from palladium, platinum, rhodium, rhenium, zirconia, copper and nickel and is carried on at least one carrier selected from alumina, silica, carbon, silica-alumina, titanium dioxide and titanium dioxide-silica. However, when a metal such as palladium, platinum, rhodium, rhenium, zirconia, copper and nickel is combined with the same as the carrier for the ruthenium catalyst, good activity and selectivity cannot be conversely obtained. Thus, the combination is not preferable. In the case that the mixed catalyst is used, the ratio between the ruthenium catalyst related to the present invention and the other metal catalysts is as follows: the ratio (ratio by weight) of the ruthenium catalyst to the other metal catalysts is preferably from 1/1 to 1/0.01, more preferably from 1/0.8 to 1/0.05.

As the method for carrying the catalyst metal onto the carrier, any ordinary method can be used. Examples thereof include a precipitation method, an immersion method, an ion exchange method, a sol-gel method, a replacement method and the like.

In the process of the present invention, the used amount of the catalyst depends on the manner of the reaction. In general, in the case of a batch manner, this amount is preferably from 0.1 to 20% by weight, more preferably from 0.5 to 10% by weight of the polyoxyalkylene triol, which is a reaction object, from the viewpoint of obtaining good reactivity and selectivity. In the case of a continuous manner, the metal is carried onto the carrier and subsequently the catalyst can be adjusted into a desired size and a desired shape. The size and the shape of particles of the catalyst are not particularly limited. For example, a form of particles or pellets having a size of 2 to 3 mm is preferred.

In the process of the present invention, it is preferable to use ammonia at a ratio such that the mole ratio of ammonia to one hydroxyl group of the polyoxyalkylene triol ($NH_3$/OH group) is from 1/1 to 15/1, more preferably from 4/1 to 11/1.

Regarding hydrogen, the mole ratio of the hydrogen to one hydroxyl group of the polyoxyalkylene triol ($H_2$/OH group) is preferably from 0.1/1.0 to 4.0/1.0 or 0.1/1.0 to 3.0/1.0, more preferably from 0.5/1.0 to 2.5/1.0 from the viewpoint of suppressing the generation of secondary amines and/or alcohol condensates and obtaining good selectivity.

The reaction of the present invention can be performed in a batch manner or continuous manner. The pressure at this time is preferably within the range of 0.1 to 15 MPa, more preferably within the range of 0.5 to 10 MPa as a gauge pressure in both of the batch and the continuous reactions. The reaction temperature is preferably from 160 to 270° C., more preferably from 180 to 240° C. from the viewpoint of obtaining a good conversion rate and suppressing the decomposition reaction or catalyst deterioration based on the reaction.

The LHSV (time space velocity of liquid) of the case of the continuous reaction is preferably 10 or less, more preferably from 2 to 10 from the viewpoint of obtaining good conversion rate.

EXAMPLES

The following examples further describe and demonstrate embodiments of the present invention. The examples are given solely for the purpose of illustration and are not to be construed as limitations of the present invention.

In the following examples, the conversion rate and the selectivity were calculated according to the following equations:

Conversion rate (%)=(total amine value)/(hydroxyl value)×100, and

Selectivity (%)=(total amine value−partial amine value)/(total amine value)×100.   (equation 1)

Selectivity of the present invention means a ratio of primary amine to the obtained amines. The production method of the present invention side-produces secondary amines and tertiary amines other than the primary amine. That is, the selectivity can be obtained by using the amount of the secondary and tertiary amines and the equation 1.

Amount of the secondary and tertiary amines (%)= (partial amine value)/(total amine value)×100

Herein, the hydroxyl value, the total amine value and the partial amine value are values obtained by measuring a reaction finish product in the following manners, respectively.

<Hydroxyl Value>

The hydroxyl value was obtained from the following equation:

Hydroxyl value=apparent hydroxyl value−acid value

The apparent hydroxyl value represents the mass of potassium hydroxide, in the unit of mg, necessary for neutralizing acetic acid bonded to hydroxyl groups in 1 g of a sample when the sample is acetylated. The measurement thereof was performed according to JIS K 0070. That is, into a flask are charged the sample and 3 mL of an acetylating reagent (a mixed solution of 40 mL of pyridine and 10 mL of acetic anhydride), and they are caused to react at 95° C. for 1 hour. Thereto is added 1 mL of water, and the system is again heated for 10 minutes. The system is cooled to room temperature, and then to the resultant solution are added 30 ml of neutral ethanol and a phenolphthalein indicator. The solution is titrated with an alcoholic potassium hydroxide standard solution having the corresponding concentration. The point at which the color of the solution is changed from colorlessness to faint red is defined as the end point. A blank is conducted to make a correction.

The acid value represents the mass of potassium hydroxide, in the unit of mg, necessary for neutralizing an aliphatic-acid-group-containing component contained in 1 g of the sample. The measurement thereof was performed according to JIS K0070-1966. That is, the sample is charged into a flask, and then to the sample are added 30 mL of a solvent wherein ethyl ether and ethyl alcohol are mixed at a ratio of 3:7, and about 1% phenolphthalein indicator solution. The solution is titrated with an alcoholic potassium hydroxide standard solution having the corresponding concentration. The point at which the color of the solution is changed from colorlessness to faint red is defined as the end point. A blank test is conducted to make a correction.

<Total Amine Value>

The total amine value is a value obtained by calculating, from an amount of hydrochloric acid necessary for neutralizing the total amount of primary amines, secondary amines and tertiary amines in 1 g of the sample, the total amount of the primary amines, the secondary amines and the tertiary amines contained in 1 g of the sample; and then converting the total amount to potassium hydroxide in the unit of mg. The measurement thereof was performed according to ASTM D 2073. That is, the sample is charged into a flask, and thereto are then added 30 mL of a solvent wherein ethyl ether and ethyl alcohol are mixed at a ratio of 3:7, and a phenolphthalein indicator solution. A potentiometric titration device is used to titrate the solution with an alcoholic hydrochloric acid solution having the corresponding concentration. The point at which the color of the solution is changed from colorlessness to faint red is defined as the end point. A blank test is conducted to make a correction.

<Partial Amine Value>

The partial amine value is a value obtained by calculating, from an amount of hydrochloric acid necessary for neutralizing the total amount of primary amines, secondary amines and tertiary amines in 1 g of the sample, the total amount of the secondary amines and the tertiary amines contained in 1 g of the sample; and then converting the total amount to potassium hydroxide in the unit of mg. The measurement thereof was performed according to ASTM D 2073. That is, the sample is put into a beaker, and then 50 mL of ethyl alcohol is added thereto so as to dissolve the sample in the alcohol. Thereto is added 5 mL of a salicylic aldehyde reagent (reagent obtained by dissolving salicylic aldehyde in ethanol, adding a BCG indicator thereto, and then neutralizing the solution with hydrochloric acid or the like). The components are caused to react at room temperature for 30 minutes. A blank test is conducted to make a correction.

External reduction treatment of a catalyst was conducted by the following method.

<External Reduction Treatment of a Catalyst>

A catalyst was charged into a reaction pot having a volume of 200 mL, and nitrogen was used to remove the air sufficiently. Thereafter, reduction treatment was conducted at a temperature of 200° C. or higher under hydrogen flow for about 2 hours to activate the catalyst. The catalyst was cooled to room temperature and was used for the reaction.

EXAMPLE 1

Into an electromagnetic induction rotating stirrer type autoclave having an inside volume of 500 mL were charged 150 g (0.05 mol) of a polyoxyalkylene triol (hydroxyl value: 55), having a molecular weight of 3000,obtained by addition-polymerizing propylene oxide to glycerin and 3 g of a 5% ruthenium-alumina powdery catalyst, manufactured by N. E. Chemcat Corp. and subjected to the external reduction treatment, as it was. Nitrogen-replacement was then conducted. Subsequently, 26 g (1.53 mol) of ammonia and hydrogen (0.18 mol) were put into the autoclave under pressure in such a manner that the total pressure would be 2.0 MPaG at room temperature (25° C.). While stirring at 1000 rpm, the system was heated up to a reaction temperature of 220° C. The initial highest pressure at the same temperature was 9.8 MPaG. The pressure dropped from 9.8 MPaG to 8.4 MPaG in 4 hours. After it was confirmed that the pressure drop stopped, the reaction was further continued for 0.5 hour. Thereafter, the system was cooled to take out the reaction product. The product was filtrated to remove the catalyst. This was heated at 110° C. under reduced pressure for 1 hour to remove ammonia and generated water, thereby yielding a polyoxyalkylene triamine having a total amine value of 51.3, a partial amine value of 0.04, and a hydroxyl value of 54.5.

EXAMPLE 2

Into an electromagnetic induction rotating stirrer type autoclave having an inside volume of 500 mL were charged 250 g (0.083 mol) of a polyoxyalkylene triol (hydroxyl value: 55), having a molecular weight of 3000,obtained by addition-polymerizing propylene oxide to glycerin and 5 g of a 2% ruthenium-alumina powdery catalyst, manufactured by Kawaken and subjected to the external reduction treatment, as it was. Nitrogen-replacement was then conducted. Subsequently, 21 g (1.23 mol) of ammonia and hydrogen (0.15 mol) were put into the autoclave under pressure in such a manner that the total pressure would be 2.0 MPaG at room temperature (25° C.). While stirring at 1000 rpm, the system was heated up to a reaction temperature of 220° C. The initial highest pressure at the same temperature was 7.6 MPaG. Hydrogen was added to make the total pressure into a constant value of 7.6 MPaG, and the reaction was continued for 6 hours. Thereafter, the system was cooled to take out the reaction product. The product was filtrated to remove the catalyst. This was heated at 110° C. under reduced pressure for 1 hour to remove ammonia and generated water, thereby yielding a polyoxyalkylene triamine having a total amine value of 51.3, a partial amine value of 0.04, and a hydroxyl value of 55.3.

EXAMPLE 3

Into an electromagnetic induction rotating stirrer type autoclave having an inside volume of 500 mL were charged 150 g (0.03 mol, hydroxyl value: 34) of a polyoxyalkylene triol, having a molecular weight of 5000,obtained by addition-polymerizing propylene oxide to glycerin and 3 g of a 5% ruthenium-alumina powdery catalyst, manufactured by N. E. Chemcat Corp. and subjected to no external reduction treatment, as it was. Nitrogen-replacement was then conducted. Subsequently, 13 g (0.76 mol) of ammonia and hydrogen (0.18 mol) were put into the autoclave under pressure in such a manner that the total pressure would be 2.0 MPaG at room temperature (25° C.). While stirring at 1000 rpm, the system was heated up to a reaction temperature of 220° C. The initial highest pressure at the same temperature was 7.1 MPaG. The pressure dropped from 7.1 MPaG to 6.4 MPaG in 4 hours. After it was confirmed that the pressure drop stopped, the reaction was further continued for 0.5 hour. Thereafter, the system was cooled to take out the reaction product. The product was filtrated to remove the catalyst. This was heated at 110° C. under reduced pressure for 1 hour to remove ammonia and generated water, thereby yielding a polyoxyalkylene triamine having a total amine value of 31.7, a partial amine value of 0.05, and a hydroxyl value of 34.1.

EXAMPLE 4

Into an electromagnetic induction rotating stirrer type autoclave having an inside volume of 500 mL were charged 150 g (0.10 mol) of a polyoxyalkylene triol (Excenol 903 manufactured by Asahi Glass Co., Ltd., hydroxyl value: 112.5), having a molecular weight of 1500,obtained by addition-polymerizing propylene oxide to glycerin, and 3 g of a 5% ruthenium-alumina powdery catalyst, manufactured by Kawaken and subjected to no external reduction treatment, as it was. Nitrogen-replacement was then conducted. Subsequently, 26 g (1.53 mol) of ammonia and hydrogen (0.15 mol) were put into the autoclave under pressure in such a manner that the total pressure would be 2.0 MPaG at room temperature (25° C.). While stirring at 1000 rpm, the system was heated up to a reaction temperature of 220° C. The initial highest pressure at the same temperature was 7.9 MPaG. Hydrogen was added to make the total pressure into a constant value of 7.9 MPaG, and the reaction was continued for 6 hours. Thereafter, the system was cooled to take out the reaction product. The product was filtrated to remove the catalyst. This was heated at 110° C. under reduced pressure for 1 hour to remove ammonia and generated water, thereby yielding a polyoxyalkylene triamine having a total amine value of 108.1, a partial amine value of 0.30, and a hydroxyl value of 116.2.

EXAMPLE 5

Into an electromagnetic induction rotating stirrer type autoclave having an inside volume of 500 mL were charged 150 g (0.05 mol) of an Excenol 230 (having a molecular weight of 3000, an ethylene oxide and propylene oxide adduct of glycerin, hydroxyl value: 55), which is a polyoxyalkylene triol, and 7.5 g of a 0.5% ruthenium-alumina powdery catalyst, manufactured by N. E. Chemcat Corp. and subjected to no external reduction treatment, as it was. Nitrogen-replacement was then conducted. Subsequently, 26 g (1.53 mol) of ammonia and hydrogen (0.15 mol) were put into the autoclave under pressure in such a manner that the total pressure would be 2.0 MPaG at room temperature (25° C.). While stirring at 1000 rpm, the system was heated up to a reaction temperature of 220° C. The initial highest pressure at the same temperature was 8.1 MPaG. Hydrogen was added to make the total pressure into a constant value of 8.1 MPaG, and the reaction was continued for 8 hours. Thereafter, the system was cooled to take out the reaction product. The product was filtrated to remove the catalyst. This was heated at 110° C. under reduced pressure for 1 hour to remove ammonia and generated water, thereby yielding a polyoxyalkylene triamine having a total amine value of 49.8, a partial amine value of 0.06, and a hydroxyl value of 53.9.

EXAMPLE 6

Into an electromagnetic induction rotating stirrer type autoclave having an inside volume of 500 mL were charged 150 g (0.05 mol, hydroxyl value: 55) of a polyoxyalkylene triol, having a molecular weight of 3000,obtained by addition-polymerizing propylene oxide to glycerin as a starting material, 2 g of a 2% ruthenium-alumina powdery catalyst, manufactured by Kawaken and subjected to no external reduction treatment, as it was, and 0.5 g of a 5% palladium-alumina powdery catalyst, manufactured by N. E. Chemcat Corp., as it was. Nitrogen-replacement was then conducted. Subsequently, 31 g (1.82 mol) of ammonia and hydrogen (0.18 mol) were put into the autoclave under pressure in such a manner that the total pressure would be 2.0 MPaG at room temperature (25° C.). While stirring at 1000 rpm, the system was heated up to a reaction temperature of 220° C. The initial highest pressure at the same temperature was 11.2 MPaG. The pressure dropped from 11.2 MPaG to 9.1 MPaG in 3 hours. After it was confirmed that the pressure drop stopped, the reaction was further continued for 0.5 hour. Thereafter, the system was cooled to take out the reaction product. The product was filtrated to remove the catalyst. This was heated at 110° C. under reduced pressure for 1 hour to remove ammonia and generated water, thereby yielding a polyoxyalkylene triamine having a total amine value of 51.8, a partial amine value of 0.09, and a hydroxyl value of 55.2.

EXAMPLE 7

Into an electromagnetic induction rotating stirrer type autoclave having an inside volume of 500 mL were charged 150 g (0.05 mol, hydroxyl value: 55) of a polyoxyalkylene triol, having a molecular weight of 3000, obtained by addition-polymerizing propylene oxide to glycerin as a starting material, 2 g of a 5% ruthenium-alumina powdery catalyst, manufactured by N. E. Chemcat Corp., as it was, and 1 g of a 5% palladium-silica-alumina powdery catalyst, manufactured by N. E. Chemcat Corp., as it was. Nitrogen-replacement was then conducted. Subsequently, 21 g (1.24 mol) of ammonia and hydrogen (corresponding to 0.18 mol) were put into the autoclave under pressure in such a manner that the total pressure would be 2.0 MPaG at room temperature (25° C.). While stirring at 1000 rpm, the system was heated up to a reaction temperature of 230° C. The initial highest pressure at the same temperature was 9.8 MPaG. Hydrogen was added to make the total pressure into a constant value of 9.8 MPaG, and the reaction was continued for 6 hours. Thereafter, the system was cooled to take out the reaction product. The product was filtrated to remove the catalyst. This was heated at 110° C. under reduced pressure for 1 hour to remove ammonia and generated water, thereby yielding a polyoxyalkylene triamine having a total amine value of 49.9, a partial amine value of 0.05, and a hydroxyl value of 54.2.

Comparative Example 1

A polyoxyalkylene triamine was yielded in the same way as in Example 2 except that a nickel-molybdenum catalyst (trade name: R-239K of a Raney type), manufactured by Nikko Rica Corp., was used as the catalyst species.

Comparative Example 2

A polyoxyalkylene triamine was yielded in the same way as in Example 2 except that a 5% rhenium-carbon powdery catalyst, manufactured by N. E. Chemcat Corp., was used as the catalyst species.

Comparative Example 3

A polyoxyalkylene triamine was yielded in the same way as in Example 2 except that a 5% ruthenium-carbon powdery catalyst, manufactured by N. E. Chemcat Corp., was used as the catalyst species.

The results (conversion rates and selectivities) obtained in Examples 1 to 7 and Comparative Examples 1 to 3, and results obtained by measuring the filtratabilities and the color tones of the resultant polyoxyalkylene triamines in the following manners are together shown in Table 1.

<Filtratability>

A commercially available filter paper (5 C, manufactured by ASVANTEC) was cut off into the form of a circle having a diameter of 2.8 cm. The circle was set into a filter, and then 300 g of each of the reaction finish products (containing the catalyst) was used as a filtrating material, and the filtratabilities of the products were compared at 90° C. under an applied nitrogen pressure of 0.3 MPa. The filtratabilities were judged from the filtration rates at 3 minutes from the start of the filtration. They were evaluated on the basis of the following criterion:

⊙: The filtration rate was larger than 5 g/minute.
○: The filtration rate was larger than 3 g/minute and smaller than 5 g/minute.
×: The filtration rate was smaller than 3 g/minute.

<Measurement of the Color Tone>

An APHA tube was used to measure, with the naked eye, the color tone (initial value) of each of the resultant polyoxyalkylene triamines and the color tone thereof after this was allowed to stand still at 160° C. under nitrogen flow for 2 hours.

As is evident from Table 1, the processes of the examples of the present invention gave good conversion rates, selectivities, and filtratabilities and the color tones of the resultant polyoxyalkylene triamines were very stable. Examples 8 to 10 and Comparative Examples 4 to 6

(1) Charging and Activating of Catalysts

Ruthenium-alumina pellet catalysts manufactured by N. E. Chemcat Corp. were used as catalysts related to the present invention, and palladium-alumina pellet catalysts manufactured by N. E. Chemcat Corp. were used as comparative catalysts. A given amount of each catalyst shown in Table 2 was charged into a reaction pot, and nitrogen-replacement was then performed. Thereafter, hydrogen was circulated into the pot, and then the temperature was raised to 200° C. After the arrival of the temperature, the temperature was kept for 2 hours to conduct a reducing operation. Thereafter, the system was cooled to room temperature and the hydrogen was changed to nitrogen.

(2) Reaction

Nitrogen was caused to flow into a continuous reaction pot (the upper and lower portions of which were filled with Raschig rings, reaction pot volume: 250 mL, catalyst amount: 100 mL) that was filled with the catalyst reduced in the above step (1) at a pressure of 0.3 MPa and a flow rate of 10 L/h. as a converted value under normal pressure. The temperature was raised. When the temperature reached 120° C., the nitrogen was changed to hydrogen. The temperature was raised to 220° C., and the pressure was raised to a given pressure. Subsequently a pump was used to charge ammonia and the same polyoxyalkylene triol (molecular weight: 3000, hydroxyl value: 55) as in Example 1 into the reaction pot. Circulating reaction was conducted at a given LHSV shown in Table 2 in such a manner that the ratio of $NH_3/OH$ and that of $NH_3/H_2$ would be given mole ratios shown in Table 2. The reaction finish product was subjected to the same dehydrating operation as in Example 1. The obtained results (the conversion rate and the selectivity), and the color tone of the resultant polyoxyalkylene triamine were measured in the same way as in Example 1. The results are together shown in Table 2

TABLE 1

| | | Conversion rate (%) | Selectivity (%) | Filtratability | Color tone (APHA) Initial value | Value after heating for 2 hours |
| --- | --- | --- | --- | --- | --- | --- |
| | Catalyst species | | | | | |
| Example | | | | | | |
| 1 | 5% Ruthenium-almina powdery catalyst | 94.1 | 99.9 | ⊙ | 15 | 20 |
| 2 | 2% Ruthenium-alumina powdery catalyst | 92.7 | 99.9 | ⊙ | 10 | 15 |
| 3 | 5% Ruthenium-alumina powdery catalyst | 93.0 | 99.8 | ⊙ | 10 | 20 |
| 4 | 5% Ruthenium-alumina powdery catalyst | 93.0 | 99.7 | ⊙ | 15 | 20 |
| 5 | 0.5% Ruthenium-alumina catalyst | 92.4 | 99.8 | ⊙ | 15 | 20 |
| 6 | 2% Ruthenium-alumina powdery catalyst 5% Paradium-alumina powdery catalyst | 93.8 | 99.8 | ⊙ | 20 | 25 |
| 7 | 5% Ruthenium-alumina powdery catalyst 5% Palladium-silica alumina powdery catalyst | 92.1 | 99.9 | ⊙ | 15 | 25 |
| Comparative example | | | | | | |
| 1 | Nickel-molybdenum catalyst of a Raney (sponged) type | 84.8 | 75.2 | × | 80 | — |
| 2 | 5% Ruthenium-carbon powdery catalyst | 90.5 | 97.5 | × | 15 | 80 |
| 3 | 5% Rhenium-carbon powdery catalyst | 54.1 | 98.7 | ○ | 10 | — |

TABLE 2

|  | Catalyst species | NH₃/OH (mole ratio) | NH₃/H₂ (mole ratio) | Pressure (MPa) | LHSV | Convertion rate (%) | Selectivity (%) | Color tone (APHA) Initial value | Color tone (APHA) Value after heating for 2 hours |
|---|---|---|---|---|---|---|---|---|---|
| Example | | | | | | | | | |
| 8 | 0.5% Ru/alumina pellet | 9/1 | 0.5/1.0 | 9.5 | 10 | 96.2 | 99.7 | 10 | 30 |
| 9 | 2% Ru/alumina pellet | 5/1 | 2.0/1.0 | 7.5 | 4 | 96.6 | 98.5 | 20 | 50 |
| 10 | 2% Ru/Alumina pellet | 7/1 | 1.5/1.0 | 8.5 | 4 | 97.1 | 98.6 | 30 | 40 |
| Comparative example | | | | | | | | | |
| 4 | 0.5% Pd/alumina pellet | 9/1 | 0.5/1.0 | 9.5 | 10 | 82.9 | 99.0 | 30 | 60 |
| 5 | 2% Pd/alumina pellet | 5/1 | 2.0/1.0 | 7.5 | 4 | 78.4 | 97.5 | 60 | 80 |
| 6 | 2% Pd/alumina pellet | 7/1 | 1.5/1.0 | 8.5 | 4 | 80.5 | 98.1 | 40 | 60 |

What is claimed is:

1. A process for producing polyoxyalkylene triamine, comprising:
bringing a polyoxyalkylene triol represented by formula (I):

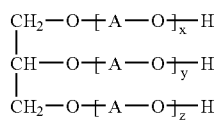

wherein A represents a normal or branched alkylene group having 2 to 6 carbon atoms, "A" may be the same as or different from one another, x, y and z are each an average mole number of alkyleneoxy groups added to each oxygen atom, and the total of x+y+z is from 1 to 100 into contact with ammonia and hydrogen in the presence of a catalyst,
wherein the catalyst comprises ruthenium metal in an amount of 0.5 to 20% by weight of the total weight of the catalyst,
the ruthenium metal is carried on at least one carrier selected from the group consisting of alumina, silica, silica-alumina, titanium dioxide and titanium dioxide-silica, and
wherein the mole ratio of the ammonia to one OH group of the polyoxyalkylene triol is from 1/1 to 11/1.

2. The process according to claim 1, wherein ammonia is used at a mole ratio of ammonia to one hydroxyl group of the polyoxyalkylene triol in the range of 4/1 to 11/1.

3. The process according to claim 1, wherein the catalyst is a mixed catalyst comprising a first catalyst comprising ruthenium metal at an amount of 0.5 to 20% by weight of the total weight of the catalyst, carried on at least one carrier selected from the group consisting of alumina, silica, silica-alumina, titanium dioxide and titanium dioxide-silica, and a second catalyst comprising at least one metal selected from the group consisting of palladium, platinum, rhodium, rhenium, zirconia, copper and nickel, carried on at least one carrier selected from the group consisting of alumina, silica, carbon, silica-alumina, titanium dioxide and titanium dioxide-silica.

4. The process according to claim 1, wherein the polyoxyalkylene triamine comprises 85% or more by weight of a compound represented by formula (II):

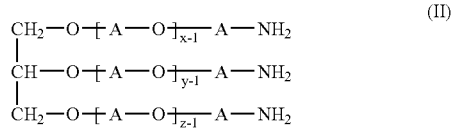

wherein A represents a normal or branched alkylene group having 2 to 6 carbon atoms, "A" may be the same as or different from one another, x, y and z are each an average mole number of alkyleneoxy groups added to each oxygen atom, and the total of x+y+z is from 1 to 100.

5. The process according to claim 1, which is performed in a continuous manner or a batch manner.

6. The process according to claim 1, wherein the mole ratio of the ammonia to one OH group of the polyoxyalkylene triol is from 1/1 to 8.4/1.

7. The process according to claim 1, wherein the mole ratio of the ammonia to one OH group of the polyoxyalkylene triol is from 4/1 to 8.4/1.

8. The process according to claim 1, wherein the polyoxyalkylene triol is brought into contact with ammonia and hydrogen in the presence of a catalyst without removing any water formed.

9. The process according to claim 1, wherein the only metal of the catalyst is ruthenium.

10. The process according to claim 1, which is a closed process.

11. The process according to claim 1, wherein the polyoxyalkylene triol has a molecular weight of from 1,500 to 5,000.

12. The process according to claim 1, wherein the catalyst is present in an amount of from 0.5 to 10% by weight based on the weight of the polyoxyalkylene triol.

13. The process according to claim 1, carried out at a temperature of from 180 to 240° C.

14. The process according to claim 1, wherein the ruthenium is present in an amount of from 0.5% to 5% by weight based on the weight of the polyoxyalkylene triol and the conversion rate of the polyoxyalkylene triol is from 92.4% to 94.1%.

15. The process according to claim 1, wherein the ruthenium is present in an amount of from 0.5% to 5% by weight based on the weight of the polyoxyalkylene triol and the carrier is alumina.

16. The process according to claim 1, wherein the ruthenium is present in an amount of from 0.5% to 5% by weight based on the weight of the polyoxyalkylene triol and the selectivity of polyoxyalkylene triamine formation is from 99.7 to 99%.

17. The process according to claim 1, wherein the catalyst is in a powdery form.

18. The process according to claim 1, wherein the catalyst comprises from 0.5 to 2% by weight of ruthenium, the carrier is alumina, and the catalyst is in the form of a pellet.

19. The process according to claim 6, wherein the conversion rate is from 96.2 to 97.1%.

20. The process according to claim 6, wherein the selectivity of polyoxyalkylene triamine formation is from 98.5 to 99.7%. mole number of alkyleneoxy groups added to each oxygen atom, and the total of x+y+z is from 1 to 100.

\* \* \* \* \*